United States Patent
Hsiao et al.

(10) Patent No.: US 6,512,382 B1
(45) Date of Patent: Jan. 28, 2003

(54) METHOD FOR CORROSION SUSCEPTIBILITY TESTING OF MAGNETIC HEADS USING SIMULATED DISK CORROSION PRODUCTS

(75) Inventors: Yiping Hsiao, San Jose, CA (US); Ciaran A. Fox, Sunnyvale, CA (US); Atul Kumar, San Jose, CA (US)

(73) Assignee: International Business Machines Corporation, Armonk, NY (US)

(*) Notice: Subject to any disclaimer, the term of this patent is extended or adjusted under 35 U.S.C. 154(b) by 0 days.

(21) Appl. No.: 09/908,034

(22) Filed: Jul. 17, 2001

(51) Int. Cl.[7] .............................................. G01R 27/08
(52) U.S. Cl. ........................................ 324/700; 324/691
(58) Field of Search ................................ 324/700, 691, 324/693; 73/86, 87

(56) References Cited

U.S. PATENT DOCUMENTS

| | | | |
|---|---|---|---|
| 4,416,709 A | 11/1983 | Ohya et al. ................ 148/403 |
| 4,467,382 A | 8/1984 | Huisman .................... 360/125 |
| 4,755,897 A | 7/1988 | Howard ...................... 360/113 |
| 4,858,049 A | 8/1989 | Kobayashi et al. ......... 360/126 |
| 4,898,774 A | * 2/1990 | Yamashita .................. 428/336 |
| 5,023,738 A | 6/1991 | Prenosil ..................... 360/122 |
| 5,315,468 A | 5/1994 | Lin et al. ................... 360/113 |
| 5,729,409 A | 3/1998 | Ohashi et al. .............. 360/113 |
| 5,864,452 A | 1/1999 | Hirano et al. .............. 360/122 |

FOREIGN PATENT DOCUMENTS

| | | |
|---|---|---|
| JP | 53-73416 | 6/1978 |
| JP | 53-104516 | 9/1978 |
| JP | 5-028476 | 2/1993 |
| JP | 11-191288 | 7/1999 |

* cited by examiner

*Primary Examiner*—Christine Oda
(74) *Attorney, Agent, or Firm*—Robert B. Martin; Lewis L. Nunnelley

(57) ABSTRACT

A method of corrosion susceptibility testing of a magnetic recording head is disclosed. The method includes applying simulated disk corrosion products containing cobalt salts to the recording head. The recording head is then placed in an environmental chamber with elevated temperature and humidity. The resistance of the sensor on the recording head is measured after removal from the chamber and compared with the resistance before placement in the chamber. A significant change in resistance indicates a corrosion failure. This component level testing gives a more accurate indication of the corrosion performance of the recording head when placed in a disk drive.

7 Claims, 1 Drawing Sheet

METHOD FOR CORROSION SUSCEPTIBILITY TESTING OF MAGNETIC HEADS USING SIMULATED DISK CORROSION PRODUCTS

BACKGROUND OF THE INVENTION

1. Field of the Invention

The present invention relates generally to magnetic recording heads used in disk drives and specifically to a method for testing the susceptibility of magnetic recording heads to corrosion.

2. Description of the Background Art

Contemporary disk drives have at least one disk for storing digital information and at least one recording head for writing and reading digital information to the disk. The disk and head both comprise materials which are susceptible to corrosion. The read back sensor on the recording head in particular is constructed with materials which can be susceptible to corrosion. The materials in the read back sensor of the head are usually covered with a thin layer of diamond like carbon (DLC) to protect against corrosion. This DLC coating is effective for corrosion protection, but is not perfect. Accordingly one of the challenges when designing and constructing magnetic recording heads is to properly evaluate the susceptibility of the materials in heads to corrosion and also the effectiveness of corrosion protection measures.

One method of testing the corrosion performance of recording heads is to build a disk drive using the heads of interest. The disk drive is then subjected to long term testing. This testing can be done at ambient conditions or in an accelerated corrosion environment of high temperature and high humidity. Very accelerated conditions can be achieved by additionally placing the disk drive in a corrosive mix of gases such as chlorine, hydrogen sulfide, etc. This method of utilizing the finished disk drives for corrosion testing is very expensive and quite slow. Also there is usually considerable uncertainty in relating results from aggressively accelerated tests to actual performance when the disk drive is in a normal use environment.

Another method of testing the corrosion performance of recording heads involves an accelerated test at the component level. In this method individual heads are placed in a corrosion testing chamber having elevated temperature and humidity. Optionally corrosive gases such as chlorine and hydrogen sulfide can also be introduced into the testing chamber. Another optional technique is to dip the heads in a saline solution before testing. The component level method is less expensive and much faster than the disk drive method. However the corrosion results from this component method correlate poorly with the results from normal operation of the disk drive. This is because the recording head during component level testing is exposed to different chemical and environmental stresses than during normal operation of a disk drive.

There is a need for a method of corrosion testing of recording heads at the component level which is fast and inexpensive and also indicates more accurately the performance in the disk drive.

SUMMARY OF THE INVENTION

One embodiment of the present invention provides for a corrosion testing method for recording heads which is fast and inexpensive. The method is based on testing components but the results correlate well with corrosion testing of recording heads inside disk drives. The method includes applying a cobalt salt to the recording head; measuring the resistance of the read element in the recording head; subjecting the recording head to elevated temperature and humidity; making a second resistance measurement of the read element; and finally, comparing the two resistance measurements. An example of one cobalt salt which may be used is cobalt sulfate. The cobalt salt may be applied to the recording head by dipping the head into a solution of the salt, by evaporating the salt onto the head, or by applying a slurry of the salt mixed with a lubricant.

Other aspects and advantages of the present invention will become apparent from the detailed description along with the drawing illustrating by way of example the principles of the invention.

DETAILED DESCRIPTION OF THE INVENTION

Figure 1:
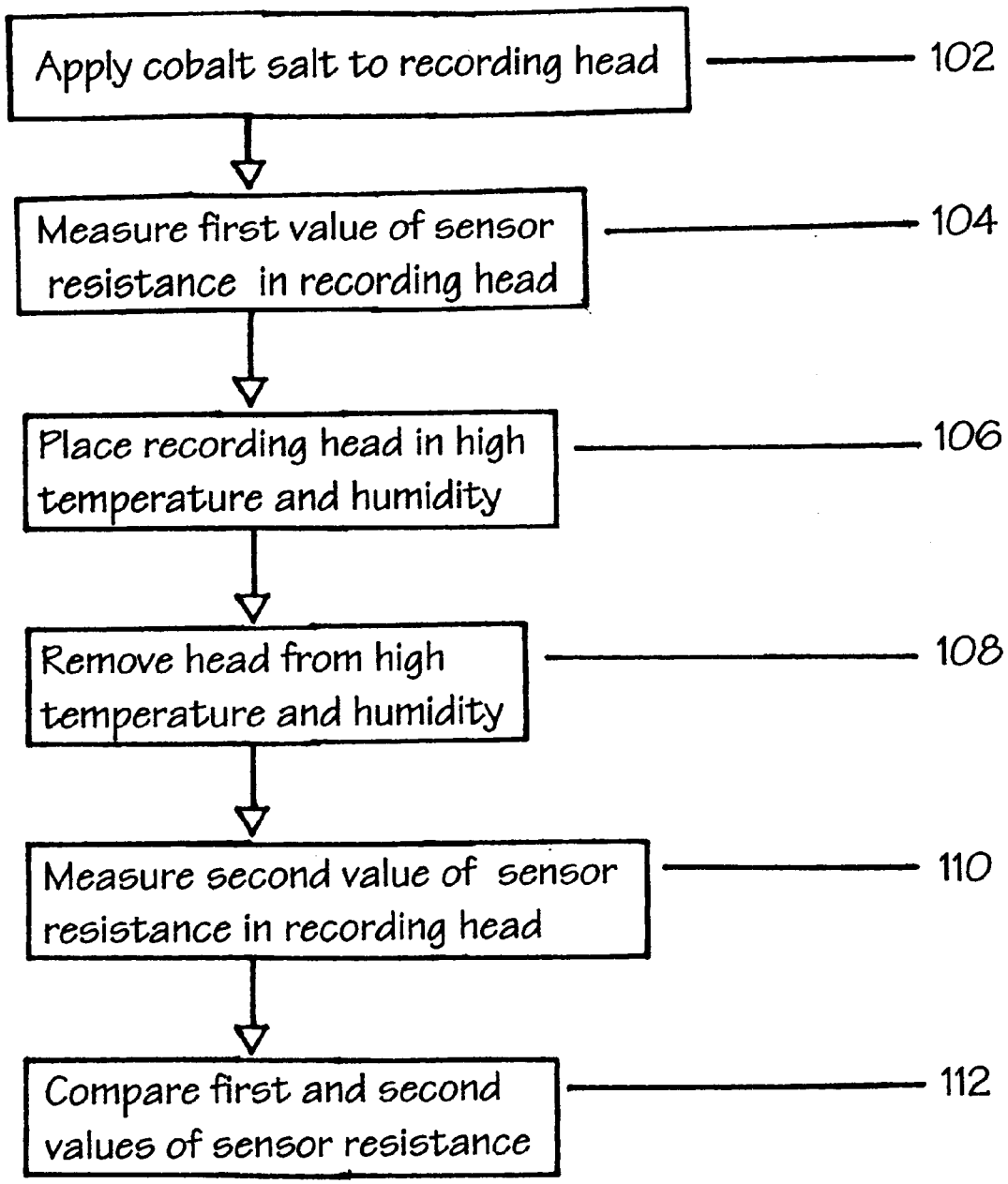
FIG. 1 shows an embodiment of the corrosion susceptibility test method.

One embodiment of the present invention provides for a corrosion testing method for recording heads which is fast, inexpensive, and correlates well with corrosion performance of recording heads inside disk drives. Previous methods of component testing do not use simulated disk corrosion products to replicate the environment inside the disk drive.

In order to determine the environment of heads during operation of a disk drive, a group of disk drives were subjected to an aggressive corrosion test by placing the disk drives in a corrosion testing chamber at elevated temperature and humidity. The recording heads, having giant magnetoresistive (GMR) sensors, were then removed and evaluated. The resistance values of the heads before and after the tests were compared. Usually the first indication that recording sensors are damaged by corrosion is an increase in resistance. The heads that increased by more than 1.0 ohm were further analyzed by examination of the corrosion products on the head with a scanning electron microscope (SEM). The SEM was capable of determining the elemental composition of the corrosion products. As used herein, corrosion products refers to the material resulting from corrosion observed on the heads after a corrosion test. This material, or set of materials, is readily observed on a corroded head as an undesirable, irregular smear or tarnish. The elemental analysis showed that over 90% of the corrosion products on the head contained cobalt salts with cobalt and sulfur as the dominant material. The most likely salt based on the elemental analysis was cobalt sulfate. Since the magnetic film in the disk has a substantial amount of cobalt and the head has very little, this surprising result indicates that disk corrosion products are on the recording head and are strongly associated with head corrosion.

The method of the present invention of testing for corrosion of the head at the component level is a better indicator of corrosion performance of the head in a disk drive. The method is involves bringing the recording head into contact with simulated disk corrosion products before assessing the corrosion susceptibility. The preferred method is to dip the head into a dilute aqueous solution of a cobalt salt. The head is then dried and placed in a corrosion chamber under preferably moderate stress. Moderate stress means an elevation in temperature and humidity but not an introduction of corrosive gasses.

The details of the corrosion test method are illustrated in FIG. 1. A number of cobalt salts are observed in disk corrosion products. These include cobalt sulfate and cobalt chloride. Cobalt sulfate is the preferred material for simulating these products. The chosen cobalt salt is applied to the recording head 102. One preferred application method is to dip the head in a moderately dilute solution of the cobalt salt. For example, a typical solution is 0.5 M cobalt sulfate with a small amount of surfactant. 0.1% liquinox is suitable as a surfactant. During the dipping operation it is preferable to provide for an electrostatic discharge (ESD) safe environment by grounding the recording heads. After dipping, excess solution is drained off the surface. The recording heads are then left to dry in ambient air.

An alternate method of applying a cobalt salt to the recording head is to evaporate the salt onto the dry head using a vacuum oven. Another alternate method of applying a cobalt salt is to dip the recording heads into a slurry containing a fine powder of the cobalt salt mixed in a lubricant. All three methods of applying the cobalt salt yield a uniform distribution of the salt on the recording head.

After application of the cobalt salt, the resistance of the recording head sensor is measured 104. The recording head is then placed in elevated temperature and humidity 106. This is most conveniently accomplished by placing the recording head in a test chamber where the temperature and humidity can be controlled. A wide range of temperature, humidity, and time combinations may be used. A typical set of chamber conditions are 80 C and 85% RH for 56 hours. After removal from the chamber 108, the resistance of the sensor in the recording head is again measured 110.

The resistance values before 104 and after 110 placing the head in the chamber are compared 112. Generally a 5 ohm change in resistance is considered a failure. A typical resistance of a sensor in a recording head is about 40 ohms. A more aggressive criterion for failure is a resistance change of 1.0 ohms. These values for resistance changes serve as guidelines and other values may be choosen.

In one test, 27 recording heads were coated with cobalt sulfate and 29 heads of the same type were used as controls. The control group were placed in the corrosion chamber along with the test group, however the control heads were not coated with the cobalt sulfate. The heads recieving the cobalt salt in the test group were dipped in a cobalt solution as described above. In the control group none of the heads had a resistance change of over 1.0 ohm. In the test group 6 of the 27 heads had a resistance change of over 1.0 ohm and 5 heads had a resistance change of over 5 ohms. This result indicates that the presence of cobalt sulfate greatly accelerates the corrosion of the sensor in a recording head. This result also indicates that the invented method has better correlation with head corrosion during normal operation inside a disk drive. Subsequent analysis of the failed heads revealed cobalt containing corrosion products at the read sensor.

From the foregoing is will be appreciated that the method of applying a cobalt salt to the recording head gives a more discriminating indication of the corrosion performance of the recording heads inside a disk drive. This allows for the rapid and inexpensive component testing of recording heads which gives results correlating well with the much more time consuming and expensive disk drive testing. While the invention has been described above in connection with preferred embodiments thereof and as illustrated by the drawing, those with skill in the art will readily recognize alternative embodiments of the invention can be easily produced which do not depart from the spirit and scope of the invention as defined in the following claims.

We claim:

1. A method for testing the susceptibility of recording heads to corrosion, comprising:

a cobalt salt to a recording head;

making a first resistance measurement of said recording head;

subjecting said recording head to elevated temperature and humidity;

making a second resistance measurement of said recording head; and, comparing said first and said second resistance measurements to determine the change in resistance.

2. A method as in claim 1 wherein said cobalt salt is cobalt sulfate.

3. A method as in claim 1 wherein said cobalt salt is applied by dipping said recording head in a solution of said cobalt salt.

4. A method as in claim 1 wherein said cobalt salt is applied by evaporation in a vacuum oven.

5. A method as in claim 1 wherein said cobalt salt is applied by applying a slurry of cobalt salt power and a lubricant.

6. A method for testing corrosion susceptibility of magnetic recording heads, comprising:

applying cobalt sulfate to a recording head by dipping the head into an aqueous solution of cobalt sulfate;

measuring a first value of sensor resistance in said recording head;

placing said recording head in a chamber at an elevated temperature and humidity;

removing said recording head from said chamber;

measuring a second value of sensor resistance in said recording head; and, comparing first and second values of sensor resistance.

7. A method as in claim 6 wherein a difference in resistance between said first and second resistance values indicates a corrosion failure.

* * * * *